United States Patent [19]

Madras

[11] Patent Number: 4,503,568
[45] Date of Patent: Mar. 12, 1985

[54] SMALL DIAMETER VASCULAR BYPASS AND METHOD

[75] Inventor: Peter N. Madras, Newton, Mass.

[73] Assignee: New England Deaconess Hospital, Boston, Mass.

[21] Appl. No.: 325,057

[22] Filed: Nov. 25, 1981

[51] Int. Cl.³ .......................... A61F 1/00; A61B 17/04
[52] U.S. Cl. ...................................... 3/1.4; 128/334 R
[58] Field of Search ................. 3/1.4, 1.5; 128/334 R, 128/303 R, 774; 604/86, 87

[56] References Cited

U.S. PATENT DOCUMENTS

| | | | |
|---|---|---|---|
| 2,924,250 | 2/1960 | Sidebotham | 3/1.4 |
| 3,620,218 | 11/1971 | Schmitt | 3/1.4 |
| 3,683,926 | 8/1972 | Suzuki | 3/1.4 |
| 3,713,441 | 1/1973 | Thomas | 128/334 C |
| 3,993,045 | 11/1976 | Ion | 128/303 R |

OTHER PUBLICATIONS

Williams, et al., "Implants in Surgery" W. B. Saunders Co. Ltd., 1973, pp. 521-524.

Primary Examiner—Richard J. Apley
Assistant Examiner—David J. Isabella
Attorney, Agent, or Firm—Lahive & Cockfield

[57] ABSTRACT

A arterial bypass includes a relatively large diameter proximal tubular segment for connection to the upstream portion of an artery and a relatively small diameter distal tubular segment for connection to the downstream portion of the artery. A tapered adapting segment joins the proximal and distal segments. The distal segment is coupled to the downstream portion of the artery by way of a connector element. The connector element includes an entrance member, a coupled, angularly offset exit member and a heel member. The exit and heel members are adapted for insertion through an arteriotomy and into the vessel. The exit member outer diameter is matched to the vessel inner diameter near the arteriotomy.

8 Claims, 13 Drawing Figures

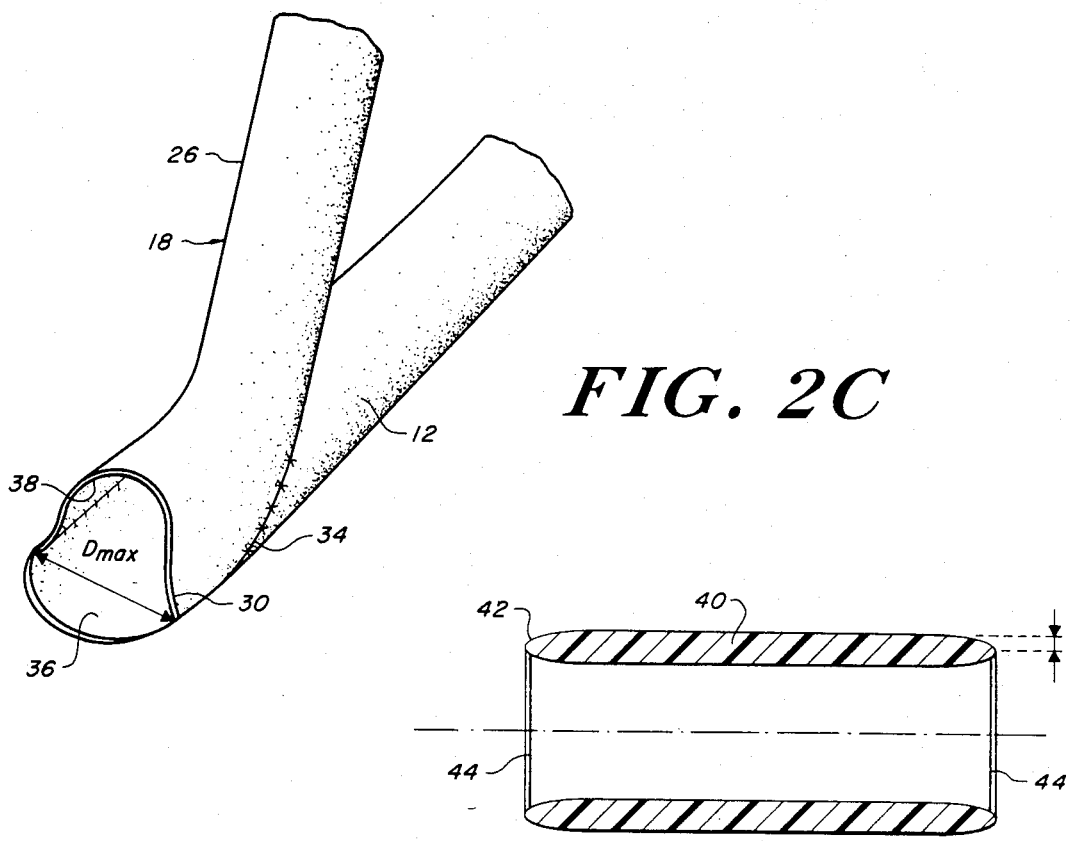
FIG. 2C
FIG. 3
FIG. 4
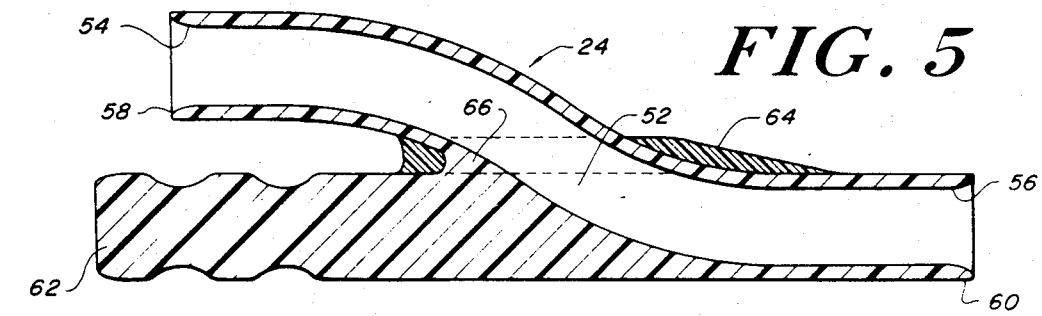
FIG. 5

SMALL DIAMETER VASCULAR BYPASS AND METHOD

This invention relates generally to vascular bypass systems and methods, and particularly to systems and methods for small diameter vascular grafting.

BACKGROUND

A number of vascular grafts occlude after months and sometimes years of apparently normal function. Such occlusion has been observed particularly for small diameter prostheses, or prostheses joined to small diameter vessels. In many cases, a characteristic hyperplastic lesion of the arterial wall has been noted at, or just beyond, the distal anastomosis. Although hyperplasia may occur at both the proximal and distal junctions, its usual manifestation is occlusion at the distal anastomosis.

While it has been generally considered that anastomotic hyperplasia in the region of the distal anastomosis is a phenomonon of unknown etiology, it now appears that a number of factors act in concert to bring about the development of this condition.

In the conventional end-to-side anastomosis (i.e. where the end of a graft tube enters the side of a vessel), there are many sources of stress at or near the junction site, including the dimensional difference between graft and vessel, the nature of the end-to-side anastomosis, and the difference in mechanical properties between graft and vessel. All of these stresses appear to be contributing factors in the development of arterial wall hyperplasia. Abnormal shear stresses continuously act upon the endothelium, leading to potential endothelial disruption. Activated blood, emerging from the prosthesis, bathes the disrupted endothelium, with resultant rapid platelet deposition. Continuous platelet deposition is another powerful stimulant to arterial hyperplasia.

It appears that size discrepancy between the prosthesis and the smaller vessel, alone, produces significant wall stress. Most vascular surgeons typically join a prosthesis with an inside diameter larger than that of the artery to the edges of a longitudinal slit in the artery. For example, an 8 mm graft might be joined to an artery of only 4 to 5 mm, with the "goal" of opening the anastomosis as widely as possible (to avoid occlusion). In fact, this practice actually leads to increased wall tension, a factor which promotes occlusion. This increase in tension is evident by considering the Laplace Law (tension=pressure×radius of curvature). Thus, the tension in the arterial segment increases as the radius of curvature of the arterial segment increases. Wall tension increases dramatically when dealing with vessels of small diameter (3 to 6 mm) where the margins needed for sutures have a significant effect on the effective radius of curvature. The foregoing considerations lead to the following criteria for the construction of small diameter vascular bypass prostheses:

1. the prosthesis must minimize or eliminate any stress to the arterial wall;
2. the normal flow patterns must be preserved;
3. the activation of blood to rapid thrombus formation must be minimized.

It is an object of this invention to provide a new and improved small diameter vascular bypass system, and a method for properly installing it, that will minimize the occlusion of small diameter vascular systems, by incorporation of the above criteria.

SUMMARY OF THE INVENTION

The invention comprises a prosthetic arterial connector element for coupling an arterial graft to a small diameter blood vessel having a arteriotomy. The connector element includes a tubular entrance member, a tubular exit member, and a heel member. The tubular entrance portion member is adapted for receiving, and providing a passage for, blood flow. The tubular exit member is coupled to and angularly offset from the tubular entrance member and provides a passage for blood from the entrance member. The tubular exit member has a downstream end adapted for insertion through the arteriotomy and into the portion of the vessel downstream of the arteriotomy. The downstream end has an outer diameter substantially equal to the inner diameter of the small diameter blood vessel at the arteriotomy.

The heel member extends substantially coaxially from the exit member. The distal end of the heel member is adapted for insertion through the arteriotomy and into the portion of the vessel upstream of the arteriotomy. In various embodiments, the heel member may be solid, or may include a passage coupled to the passages in the entrance and exit members.

In preferred embodiments, the outside diameter of the tubular exit member is equal to the inside diameter of the small diameter blood vessel opening ±0.15 mm. A throat portion is located intermediate the tubular entrance and exit members and a circumferential skirt substantially surrounds that throat portion. The skirt is adapted to heal into the advential tissue of the blood vessel.

The invention also comprises an arterial bypass system for bypassing an occluded segment of a small diameter blood vessel. The system includes a tubular segment having a relatively large diameter for connection to the blood vessel upstream of the occluded segment, a distal tubular segment having a relatively small diameter for connection to the blood vessel downstream of the occluded segment, and a tapered adapting tubular segment coupling the proximal and distal segments. The tapered segment tapers in diameter from a diameter substantially equal to the diameter of the proximal segment, to a diameter substantially equal to the diameter of the distal tubular segment. A prosthetic arterial connector element, as described above, couples the distal segment to the occluded vessel through an arteriotomy in that vessel downstream of the occluded segment.

The method of the invention for determining the inside diameter of a small blood vessel comprises the steps of placing over the vessel successively smaller calibrated collars until a first collar indents the blood vessel wall, making an aperture (such as a lateral arteriotomy) in the sidewall of severing the vessel, placing the next smaller calibrated collar over the vessel, and inserting into the vessel successively larger calibrated cylindrical probes until a probe encounters the resistance of the next smaller calibrated collar.

BRIEF DESCRIPTION OF THE DRAWING

Other objects, features and advantages of the invention will be pointed out, or will be inherent, in the following description of preferred embodiments of the invention, including the drawings thereof, in which:

FIGS. 2, 2a, 2b, 2c show the anastomosis for connecting the proximal arterial segment of the bypass system to the femoral artery;

FIG. 3 is a sectional view of the connecting link of the bypass system of FIG. 1;

FIG. 4 is a sectional view of the adapting segment of the bypass system of FIG. 1;

FIG. 5 is a sectional view of the distal arterial connector for connecting the distal arterial segment of the bypass system of FIG. 1 to the femoral artery;

DESCRIPTION OF THE PREFERRED EMBODIMENT

Figure 1:
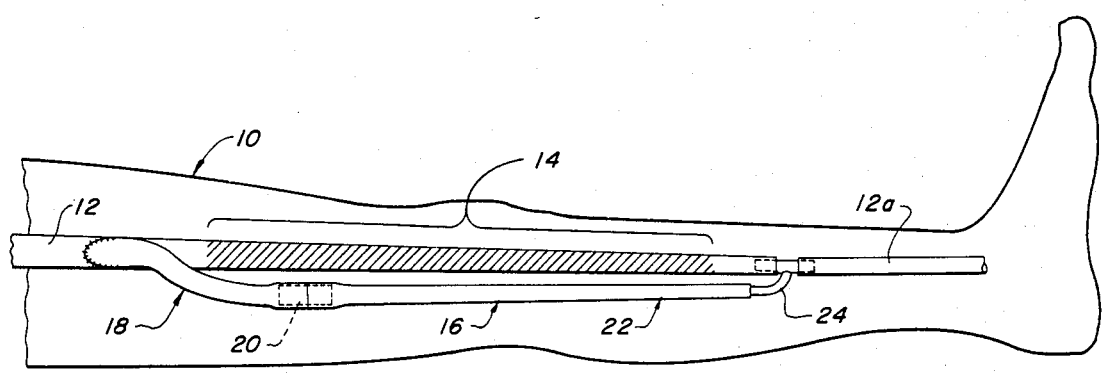
FIG. 1 is a representation, in somewhat diagrammatic form, of a bypass system used as a femorotibial bypass in a human leg.

FIG. 1 shows a human leg 10 with an artery, the common femoral artery 12, that has an occluded portion 14. A graft system 16 couples the femoral artery 12 to the tibial artery 12a, bypassing the occluded portio 14. The graft system 16 includes a proximal arterial segment 18, a connecting link 20, an adapting segment 22, and a distal arterial connector 24.

Figure 2:
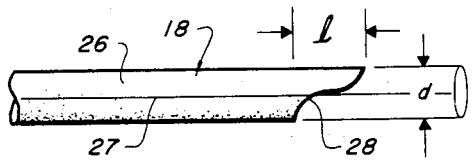
Figure 2A:
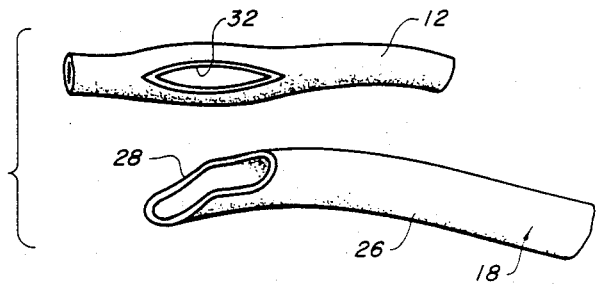
Figure 2B:
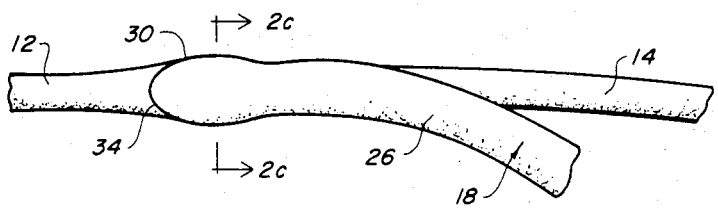

Since the graft bypass system 16 includes an upstream end originating from a relatively large vessel (i.e., the common femoral artery 12), the conventional surgical technique for an end-to-side anastomosis is shown in this embodiment. The proximal arterial segment 18, used for the end-to-side anastomosis, is a generally cylindrical tubular prosthesis 26 of a variety of materials, such as polyurethane, with a radiopaque stripe. Other materials, such as Teflon might also be used. The prosthesis 26 has a thickness and other physical properties that match the artery 12. The proximal end 28 of the prosthesis 26 is cut in the fashion illustrated in FIG. 2. That is, an "S" curve is sliced through the proximal end 28 for a distance, "l", about one-and-a-half times the diameter, "d", of the prosthesis 26. This allows the cut end of the graft to open in a somewhat splayed manner giving the "cobra head" configuration 30 that is sutured to a corresponding longitudinal arteriotomy (or slit) 32 made in the side of the artery 12 (See FIG. 2a). The result is the sutured joint 34 shown in FIG. 2b. FIG. 2c is a partly sectional view and partly perspective of the joint 34. The lower arterial portion 36 of the joint 34 is seen to be the arterial circumference opened up to meet the upper prosthetic portion 38 of the joint. The diameter (designated $D_{max}$ in FIG. 2c) of the joint 34 may be considerably larger than the diameter of the vessel 12 because of the curved configuration of the cut made in the end 28 of the prosthesis 26.

In the preferred embodiment, the connecting link 20 is an etched sleeve 40 (e.g. made of Teflon) with tapered edges 42 and a radio-opaque circular marker 44 at each end (see FIG. 3). The outside diameter of the sleeve 40 is minimally larger than the inside diameter of the proximal arterial segment 18 and the adapting segment 22, so that a tight fit is made when the proximal arterial segment 18 and the adapting segment 22 are forced onto the respective ends of the sleeve 40.

The adapting segment 22 (see FIG. 4) joins the connecting link 20 to an entrance port 54 of the distal arterial connector 24. The adapting segment 22 tapers at its distal end to fit over the outside diameter of port 54. In the preferred embodiment, the adapting segment 22 has a central tapering section 44 occupying a relatively short length, about 10 cm, a section 46 of constant diameter (e.g., about 6 mm) approximately 30 cm long on the proximal (upstream) side, and a section 48 of constant diameter (e.g., about 2 mm) approximately 30 cm long on the distal (downstream) side. The elasticity and wall thickness of the adapting segment 22 corresponds to that of a natural artery at a mean arterial pressure of 90 mm Hg. Thus a difference in wall properties will occur along the region of narrowing of this segment 22 to correspond to the reduction in dimensions of the natural artery 12 the further down the leg 10 it extends. The adapting segment 22 also has a radio-opaque stripe 50, so that its position may be ascertained post-operatively by X-ray.

The proximal end of the adapting segment 22 is united by the connecting link 20 to the proximal arterial segment 18. The tapering section 44 may be closer to the distal arterial connector 24 to minimize the length of the small diameter section 48. This placement is not critical, as long as the tapering section 44 does not overlap the distal connector 24.

As shown in FIG. 5, the distal arterial connector 24 has a main body 52 providing a blood flow passage between an entrance port 54 and an exit port 56. The entrance port 54 provides a smooth transition from the adapting segment 22 to the connector 24. The outside diameter of the entrance port 54 is selected in relation to the inside diameter of the adapting segment 22 so that a tight fit is made when the connector 24 is inserted into the adapting segment. The edges 58 of the entrance port 54 are curved to minimize discontinuity.

The outside diameter of the exit port 56 is selected to be substantially equal to the inside diameter of the artery 12a. The tolerance is selected so that the arterial wall is not stretched by more than 10%, for example ±0.15 mm in a 1.5 mm artery. To achieve this accuracy, a method of arterial calibration to be described later is used.

The material of the distal arterial connector 24 is Teflon, tapered and rounded at the edges 58 as finely as possible. The end 60 of the exit port 56 of the connector 24 is preferably of microporous Teflon. The connector 24 effectively produces an end-to-end anastomosis using a longitudinal arteriotomy and maintaining continuity of the artery 12a. Continuity is essential to ensure physiological tension in the arterial wall.

The distal arterial connector 24 includes a connector heel 62 extending upstream from the exterior of the connector tubular body 52. Preferably it is made of solid Teflon and is used to anchor the connector 24 to the downstream end of the occluded artery 14. When that end of artery 14 is tied to the heel 62, that connection absorbs the stresses of anchoring the connector 24 and prevents the stresses from occurring at the connection of the exit port 56 to the artery 12a.

A circumferential skirt 64 is coupled to and surrounds the neck 66 of the entrance port 54 of the connector 24, where the entrance port 54 merges with the exit port 56 and the heel 62. The skirt 64, for example, made of coarsly woven Dacron, will promote "healing" (i.e. ingrowth) of the adventital tissue surrounding the connector 24, eventually also assuming the role of anchoring the connector 24. As the advential tissue heals into the skirt 64, it also heals into the end of section 44 assuring a hemostatic seal at that point.

The outer diameter of the exit port 56 of the connector 24, as stated above, is substantially equal to the inner diameter of the opening of the artery 12a at the point where the artery is severed for insertion of the connector 24. Preferably, the outside diameter of available exit port sizes would be in increments of 0.33 mm for diameters between 2 and 5 mm and in increments of 0.5 mm for diameters between 5 and 8 mm.

The method of determining the inside diameter of the artery 12a so that a proper size connector 24 may be chosen is illustrated in FIGS. 6–9. The method uses a series of calibrated tools 68, having handles 70 and U-shaped collars 72 having an inside surface 74 comprising a semi-circle 76 with parallel oppositely facing sides 78 extending therefrom. The oppositely facing sides 78 are spaced apart, in the series of tools 68, at distances or gaps increasing in increments corresponding to the connector sizes, i.e., between 2 and 5 mm, in increments of 0.33 mm.

Figure 6:
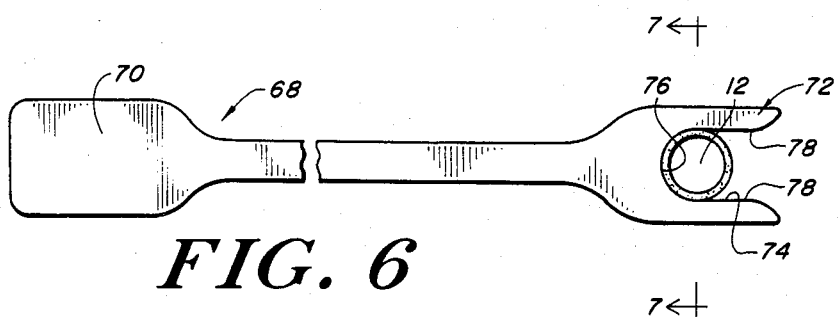
FIG. 6 shows a calibrated U-shaped collar being placed over an artery as part of a method to measure the artery's dimensions.
Figure 7:
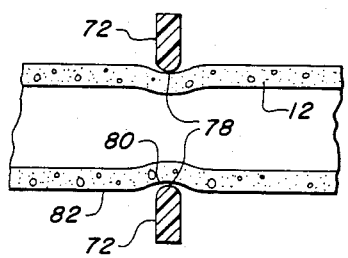
FIG. 7 is a sectional view of the artery and collar of FIG. 5, along the lines 7—7 of FIG. 6.
Figure 8:
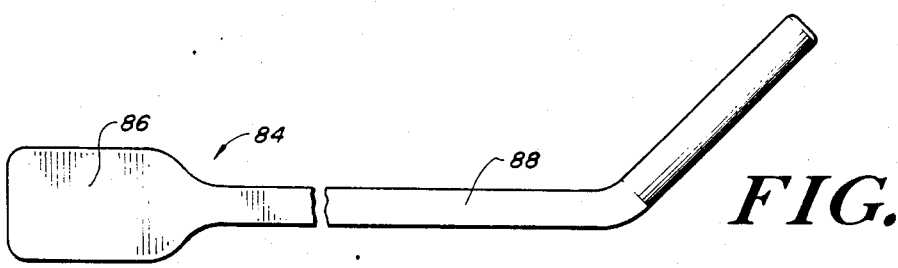
FIG. 8 shows a calibrated cylindrical probe also used as part of the measuring method.
Figure 9:
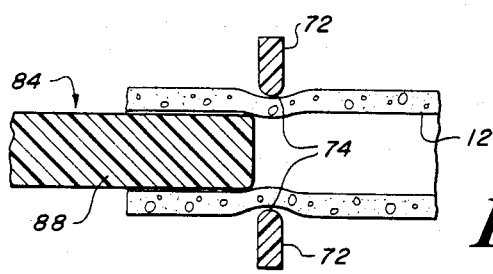
FIG. 9 is a sectional view of the artery, a collar and a probe, illustrating a step of the measuring method.

In practicing the method, tools 68 with successively smaller gaps are placed over the artery 12 to be measured (the artery 12a must be maintained wet during the measuring) until an indentation 80 in the arterial wall 82 is noticed (See FIGS. 6 and 7). The measuring is performed under magnification (for example 3.5x), and the indentation 80 may be noticed by a change in the light reflected from the arterial wall 82. The measurement is made at the expected resting point of the tip of the exit port 56 of the connector 24 which will be inserted. The surgeon declares the size of the gap. Then a longitudinal arteriotomy is performed just upstream of the measurement site.

The tool 68 with the next smaller gap is then placed over the artery 12a at the point of measurement. The next step uses a series of probes 84 having handles 86 connected to rods 88, preferably made of Teflon, with outside diameters calibrated in increments of 0.333 mm from 1.67 mm to 5 mm (See FIG. 8). Successively larger probes 86 are passed into the arteriotomy (See FIG. 9) until one encounters the slightest resistance from the collar 72 of the tool 68 being held on the artery 12a. It is assumed that this size probe 84 would pass easily if the next size tool 68 (whose size the surgeon declared) were in place. This probe 84 is therefore declared to determine the arterial inner diameter.

The appropriate size connector 24 is then fit to the adapting segment 22, which is connected to the remaining proximal portions 18 and 20 of the bypass system 16. The connector 24 is then merely placed into the artery 12a through the arteriotomy so that the connector skirt 64 butts up against the end of the arteriotomy. The heel 62 of the connector 24 is sealed by tying non-absorbable sutures (not shown) around the heel 62 in the artery 12.

The connector 24 just described is a unidirectional connector in the sense that it is designed to facilitate blood flow in a direction along the major tubular body 52 from the graft system 16 through the entrance port 54 and then the exit port 56 and into the non-occluded portion of the artery 12a.

Figure 10:
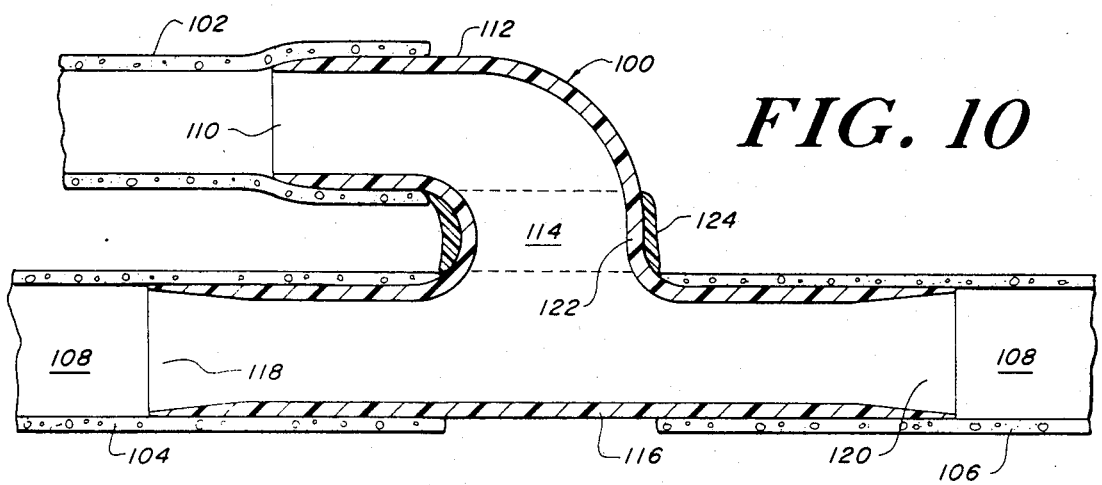
FIG. 10 is an alternative, bi-directional, embodiment of the connector shown in FIG. 5.

A bi-directional connector 100 is shown in FIG. 10. Such a connector 100 would facilitate blood flow from a graft system portion 102 into both sides 104, 106 of a severed artery 108.

The connector 100 is designed to impart minimal or zero force to the wall of the artery 108 and to recreate normal flow patterns so as to minimize shear-related endothelial damage. The connector 100 is fabricated preferably of a material like that sold under the trademark Teflon for ease of handling and hemocompatibility.

The connector 100 includes an entrance port 110 comprising a tubular portion 112, about 2 mm in diameter, for example. The tubular portion 112 terminates in a throat 114 that has a diameter of 3 mm if the entrance port 110 has a diameter of 2 mm. The throat 114 merges, end-to-side, with the mid-point of another tubular portion 116 having a diameter, to continue the example, of 2 mm. This tubular portion 116 would have a length of 1 cm, approximately. The general configuration of the connector 100 is that of a T, with the leg of the T bent to accommodate the connector to the direction of the graft system 102.

The tubular portion 116 has exit ports 118 and 120 at opposite ends for insertion into the separate portions 104 and 106, respectively, of the artery 108. The exit ports 118 and 120 are chosen to be 2 mm because the severed artery 108 has been measured, by the method described above, to have a 2 mm inner diameter, so that exit port 118 matches in diameter the first opening of the severed artery in one portion 104 and the other exit port 120 matches the second, opposite, opening of the severed artery, in the other portion 106. The tubular portion 116 of the connector 100 in the vicinity of the exit ports 118 and 120 is completely flaccid, to accommodate the artery 108. The throat 114 has a wall 122 that has a minimal rigidity.

Finally, a circumferential skirt 124 made of a material like that sold under the trademark Dacron, surrounds the throat wall 122. The skirt 124 will "heal" into the advential tissue of the artery 108, to anchor the connector 100.

The distal anastomosis is ordinarily more vulnerable to hyperplasia than the proximal. The distal vessel is smaller, and therefore higher stresses are caused in the vascular wall. Also, the blood perfusing the proximal anastomosis has contacted no foreign surface first. In addition, because the distal vessel is smaller, an equivalent degree of vascular hypertrophy will have a proportionately greater effect. Therefore the connector described in the illustrative embodiments is described as one used in a distal anastomosis. Clearly, the connector can be adapted to a proximal anastomosis as well. Other adaptations, or modifications of the illustrative embodiments will occur to those skilled in the art and will be within the scope of the invention, as set forth in the following claims:

I claim:

1. A non-absorbable prosthetic arterial connector for coupling an arterial graft to a small diameter blood vessel having an arteriotomy, said vessel having a diameter D at said arteriotomy, comprising:

a tubular entrance member adapted for receiving, and providing a passage for, blood from a prosthetic blood vessel, a tubular exit member being coupled to said entrance member and adapted for receiving and providing a passage for blood from said entrance member, the downstream end of said exit member passage being angularly offset from the downstream end of said entrance member passage, said exit member downstream end being adapted for insertion through said artiotomy and into the portion of said vessel downstream of said artiotomy, said exit member downstream end having an outer diameter D, and a heel member extending substantially coaxially from the end of said exit member opposite said exit member downstream end, said heel member having a distal end adapted for insertion through said arteriotomy and into the portion of said small diameter blood vessel upstream of said arteriotomy, wherein the central axes of the upstream portion of said entrance member and said exit member downstream end are substantially parallel.

2. The arterial connector element of claim 1 in which the outside diameter of said downstream end is equal to D±0.15 mm.

3. The arterial connector element of claim 1, including a circumferential skirt element coupled to and substantially surrounding said entrance member near the junction of said entrance member and said exit member, said skirt including means for promoting ingrowth of the advential tissue.

4. The arterial connector element of claim 1 wherein said heel member is solid and includes means for preventing the passage of blood therethrough.

5. The arterial connector element of claim 1 wherein said heel member is tubular and is adapted for receiving and providing a passage for blood from said exit member, said distal end of said heel member having an outer diameter substantially equal to D.

6. The arterial connector element of claim 1 in which the outside diameter of said distal end of said heel member is equal to D±0.15 mm.

7. An arterial bypass system for bypassing an occluded segment of a small diameter blood vessel, comprising;
a proximal tubular segment for connection to said blood vessel upstream of said occluded segment,
a distal tubular segment for connection to said blood vessel downstream of said occluded segment, said distal tubular segment having a smaller diameter than said proximal tubular segment,
a tapered adapting tubular segment coupled between said proximal and distal segments, said tapered adapting tubular segment tapering in diameter from an upstream end portion having a diameter substantially equal to the diameter of said proximal tubular segment, to a downstream end portion having a diameter substantially equal to the diameter of said distal tubular segment, and a distal arterial connector element for coupling said distal tubular segment at an arteriotomy at a point in said blood vessel downstream of said occluded segment and having a diameter D, said connector element including:
a tubular entrance portion adapted for receiving, and providing a passage for, blood from said distal segment,
a tubular exit member coupled to said entrance member and adapted for receiving, and providing a passage for, blood from said entrance member, said exit member passage being angularly offset from said entrance member passage, said exit member having a downstream end adapted for insertion through said arteriotomy and the portion of said small diameter blood vessel downstream of said arteriotomy, said downstream end having an outer diameter substantially equal to D, and
a heel member extending sustantially coaxially from the end of said exit member opposite said downstream end, said heel member having a distal end adapted for insertion through said arteriotomy and into the portion of said small diameter blood vessel uptstream of said arteriotomy,
wherein the central axes of the upstream portion of said entrance member and the downstream portion of said exit member are substantially parallel.

8. A method of determining the inside diameter of a small blood vessel at the measurement site comprising the steps of
placing and then removing over said vessel at said measurement site successively smaller calibrated collars until a first collar indents the blood vessel wall,
making an arteriotomy in the sidewalls of the vessel,
placing the next smaller calibrated collar over said vessel,
inserting through said aperture and into said vessel successively larger calibrated cylindrical probes until a probe encouters the resistance of said next smaller calibrated collar whereby the diameter of said last inserted probe is representative of the inside diameter of said small blood vessel.

* * * * *